US012235337B2

(12) United States Patent
Klomp et al.

(10) Patent No.: US 12,235,337 B2
(45) Date of Patent: Feb. 25, 2025

(54) MRI SYSTEMS AND RECEIVE COIL ARRANGEMENTS

(71) Applicants: Tesla Dynamic Coils BV, Zaltbommel (NL); Futura Composites B.V., Heerhugowaard (NL)

(72) Inventors: Dennis Wilhelmus Johannes Klomp, Heerhugowaard (NL); Catalina Sofia Arteaga de Castro, Zaltbommel (NL); Martino Borgo, Heerhugowaard (NL); Thijs van Hooren, Zaltbommel (NL); Wout Schuth, Heerhugowaard (NL)

(73) Assignees: TESLA DYNAMIC COILS BV, Zaltbommel (NL); FUTURA COMPOSITES B.V., Heerhugowaard (NL)

( * ) Notice: Subject to any disclaimer, the term of this patent is extended or adjusted under 35 U.S.C. 154(b) by 239 days.

(21) Appl. No.: 17/854,779

(22) Filed: Jun. 30, 2022

(65) Prior Publication Data
US 2023/0400541 A1    Dec. 14, 2023

(30) Foreign Application Priority Data

Jun. 13, 2022 (GB) ...................................... 2208591

(51) Int. Cl.
*G01R 33/3415* (2006.01)
*A61B 5/00* (2006.01)
(Continued)

(52) U.S. Cl.
CPC .......... *G01R 33/3415* (2013.01); *A61B 5/055* (2013.01); *G01R 33/34007* (2013.01);
(Continued)

(58) Field of Classification Search
CPC ........................................ G01R 33/34046–343
See application file for complete search history.

(56) References Cited

U.S. PATENT DOCUMENTS 4,791,371 A    12/1988   Krol
6,636,040 B1*  10/2003   Eydelman .......... G01R 33/3415
                                              324/318
(Continued)

FOREIGN PATENT DOCUMENTS

DE    10 2021 202 912 A1    4/2022
EP         3995845 A1       5/2022
(Continued)

OTHER PUBLICATIONS

Search Report under Section 17 for corresponding Great Britain Patent Application No. GB2208591.4, dated Oct. 27, 2022.
(Continued)

*Primary Examiner* — Carolyn A Pehlke
(74) *Attorney, Agent, or Firm* — McCormick, Paulding & Huber PLLC

(57) ABSTRACT

An MRI system receive coil arrangement 3 for use with a main MRI scanner arrangement, the receive coil arrangement 3 including support structure and at least one receives coil 7 carried on the support structure 40. The support structure 40 includes a receive coil housing portion 43 which defines a channel portion 43a which houses at least a portion of the at least one receive coil 7. The channel having a mouth 43b for allowing the introduction of said at least a portion of the at least one receive coil 7 through the mouth 43b and into the channel 43a and a closing portion 45 moveable between a first position in which the mouth 43b of the channel portion is open for allowing introduction of the at least a portion of the at least one receive coil 7 into the channel portion 43a and a second, closing, position in which the mouth 43b of the channel is blocked by the closing portion 45.

27 Claims, 13 Drawing Sheets

(51) Int. Cl.
*A61B 5/055* (2006.01)
*G01R 33/34* (2006.01)
*G01R 33/385* (2006.01)

(52) U.S. Cl.
CPC ... *G01R 33/34084* (2013.01); *G01R 33/3858* (2013.01); *A61B 5/4064* (2013.01)

(56) References Cited

U.S. PATENT DOCUMENTS

| | | | |
|---|---|---|---|
| 7,526,330 | B1 | 4/2009 | Randall et al. |
| 9,702,949 | B2 | 7/2017 | Jeong et al. |
| 2005/0107686 | A1 | 5/2005 | Chan et al. |
| 2006/0052685 | A1 | 3/2006 | Cho et al. |
| 2010/0239066 | A1 | 9/2010 | Fahrig et al. |
| 2012/0161769 | A1* | 6/2012 | Banerjee ............ G01R 33/3415 324/318 |
| 2013/0317346 | A1 | 11/2013 | Alagappan et al. |
| 2015/0168511 | A1 | 6/2015 | Jeong et al. |
| 2017/0312545 | A1* | 11/2017 | Panther .................. A61B 5/704 |
| 2018/0136293 | A1* | 5/2018 | Xie .................. G01R 33/34007 |
| 2021/0121066 | A1* | 4/2021 | Rheineck ......... G01R 33/34007 |
| 2022/0268864 | A1 | 8/2022 | Iwasawa et al. |

FOREIGN PATENT DOCUMENTS

| | | |
|---|---|---|
| GB | 2600919 A | 5/2022 |
| JP | H05123310 | 5/1993 |

OTHER PUBLICATIONS

European Search Report for corresponding European Patent Application No. 22181532.7, dated Dec. 14, 2022.

\* cited by examiner

MRI SYSTEMS AND RECEIVE COIL ARRANGEMENTS

CROSS-REFERENCE TO RELATED APPLICATION

This application claims foreign priority benefits under U.S.C. § 119 from British Patent Application No. 2208591.4, filed Jun. 13, 2022, the content of which is hereby incorporated by reference in its entirety.

TECHNICAL FIELD

This invention relates to MRI systems including receive coil arrangements and to receive coil arrangements for use in MRI systems as well as in some embodiments, combined systems such as MR-Linac and PET-MR systems where there is an MRI system used in combination with another system which relies on a source of radiation.

BACKGROUND

An MRI system typically comprises a main MRI scanner arrangement, a patient support or bed on which a patient lies during scanning and in at least some cases a separate, local, receive coil arrangement (or body part specific receive coil) which is arranged for location in the region of a particular body part which it is desired to scan.

The main MRI scanner arrangement typically comprises a main magnet, gradient coils, RF transmit coils, and receive coils all arranged in a main unit with a bore in which the patient is positioned during scanning. Where present, a body part specific receive coil will typically also be positioned in the bore during scanning.

As is well known MRI (magnetic resonance imaging) systems are widely used for imaging subjects and can also be used in combination systems such as MR-Linac and PET-MR systems. These combine magnetic resonance imaging with other techniques making use of radiation say for treatment, say in MR-Linac or to provide functional imaging say in PET-MR. In MRI operation, the magnet creates a large static magnetic field $B_0$, the RF transmit coils generate an alternating magnetic field $B_1$ and the receive coils, whether provided in the main unit or in a body part specific receive coil are arranged for collecting a magnetic resonance signal (that is to say acquiring magnetic resonance data). The gradient coils are used to allow spatial encoding on the $B_0$ field to enable tomographic imaging.

When an MRI system is operated using just the receive coils provided in the main unit of the scanning apparatus, the resolution and accuracy of the results can be limited in some cases. This leads to the use of separate, one may say local, receive coils, say body part specific coils as mentioned above which aim to improve imaging of a selected location/body part.

However there are limitations with existing body part specific receive coil arrangements. These include that it may be a cumbersome operation to position the receive coil arrangement around the specific body part or position the specific body part in the arrangement and/or the receive coil arrangement may give inadequate imaging results for an area of interest and/or the receive coil arrangement may be incompatible with the use of other systems such as systems using a source of radiation, for example, a linear accelerator or positron emission tomography system.

A further issue is the ease of manufacture and/or set up of such receive coil arrangements whilst facilitating for example production of arrangements with desired properties such as say shape, operational receive performance, or radio transparency.

Thus, it would be desirable to provide MRI system receive coil arrangements which are aimed at addressing at least one of these issues as well as MRI systems and combined therapy and/or imaging systems which include such an MRI system receive coil arrangement.

SUMMARY

According to a first aspect of the invention there is provided an MRI system receive coil arrangement for use with a main MRI scanner arrangement, the receive coil arrangement comprising support structure and at least one receive coil carried on the support structure, wherein the support structure comprises:
  a receive coil housing portion which defines a channel portion which houses at least a portion of the at least one receive coil, said channel having a mouth for allowing the introduction of said at least a portion of the at least one receive coil through the mouth and into the channel; and
  a closing portion moveable between a first position in which the mouth of the channel portion is open for allowing introduction of said at least a portion of the at least one receive coil into the channel portion and a second, closing, position in which the mouth of the channel is blocked by the closing portion.

This provides a convenient way to allow the production of an appropriately shaped and dimension support structure and subsequently the introduction and retention of the desired receive coil(s). It can also help avoid the need for processing of the material of the support structure in securing the desired receive coils—for example it can avoid the use of heating, use of adhesives, or the application of a second material to a base material of the support structure—eg avoid the need to coat a base material plus coil portions with a foam material. This in turn can be helpful since it increases flexibility in choice of materials for the support structure—compatibility with heating, adhesives etc. need not be considered—rather the material can be selected based on its suitability for supporting the receive coil(s) and suitability for use in MRI and companion processes/treatments that may be used alongside MRI.

Further this arrangement facilitates production of a housing portion in which deformation of the housing portion by a user is possible as the closing portion is moved to the closed position and in which moving of the closing portion into the closed position can serve to hold the housing portion in said deformed position. This in turn can allow subtle adjustment of the relative position of the at least one receive coil carried in the housing portion which can be used to fine tune the response of the receive coil.

In such an arrangement the channel portion and closing portion may co-operate together to retain the at least one receive coil. The channel portion may hold the at least one receive coil in a desired position. The closing portion may assist in holding the at least one receive coil in a desired position. The interaction between the channel portion and closing portion may assist in holding the at least one receive coil in a desired position.

The closing portion may be a push fit closing portion which is push fittable into the second, closed, position from the first position.

This helps to further enhance convenience by providing a simple way to secure the closing portion in the closed position.

The support structure may be arranged so that the closing portion is locked against movement back towards the first position once moved, for example push fitted, into the second position.

The locking may be releasable. Thus in other words—The support structure may be arranged so that the closing portion is releasably locked against movement back towards the first position once moved, for example push fitted, into the second position.

The support structure may be arranged so that the closing portion latches into the second position.

Amongst other things, these features can help enhance the provision of a housing which facilitates adjustment of the positioning of carried receive coils as the receive coil arrangement is assembled.

In one set of embodiments the closing portion may be arranged to be a push fit with the housing portion, such that in moving the closing portion to the closing position, the closing portion is push fitted into position on the housing portion and blocks the mouth of the channel portion.

The closing portion may be arranged to be a push fit with the mouth of the of the channel portion. The closing portion may be arranged to be push fittable into the mouth.

In another set of embodiments the closing portion may comprise first and second engaging portions which are a push fit with one another, such that in moving the closing portion to the closing position, the first and second engaging portions are push fitted together to block the mouth of the channel portion.

In either or both of the above sets of embodiments, the support structure may be arranged so that at least one of:
 i) the closing portion is locked against movement back towards the first position once push fitted into the second position;
 ii) the closing portion is releasably locked against movement back towards the first position once push fitted into the second position; and
 iii) the closing portion latches into the second position.

The closing portion and the housing portion may be arranged so that at least one of:
 i) the closing portion is locked against movement back towards the first position once push fitted into position on the housing portion;
 ii) the closing portion is releasably locked against movement back towards the first position once push fitted into position on the housing portion; and
 iii) the closing portion latches into position on the housing portion.

The first and second engaging portions of the closing portion may be arranged so that at least one of:
 i) the closing portion is locked against movement back towards the first position once the first and second engaging portions are push fitted together;
 ii) the closing portion is releasably locked against movement back towards the first position once the first and second engaging portions are push fitted together; and
 iii) the first and second engaging portions latch together when they are push fitted together.

The mouth of the channel portion may have a receiving region which has a re-entrant shape in cross-section and the closing portion may comprise a correspondingly shaped insertion portion which fits in the receiving region when the closing portion is push fitted into the mouth.

For the avoidance of doubt, the following features are equally applicable to each of the two sets of embodiments mentioned above and in general.

The closing portion may be integral with housing portion.

The closing portion may be a separate component from the housing portion.

The closing portion may be connected to the housing portion when in the first position.

The closing portion may be separate from the housing portion when in the first position.

The housing portion may be shaped so as to conform with a predetermined body part. If say the receive coil arrangement is designed for use in scanning a patient's head and/or neck, the housing portion may be shaped so as to fit over and around at least part of a patient's head and/or neck.

In some instances the support structure may comprise a base portion and a cover portion. The base portion may be more rigid than the cover portion. The cover portion may comprise said receive coil housing portion.

Preferably the receive coil arrangement comprises a plurality of receive coils carried on the support structure.

Preferably the receive coil housing portion houses a plurality of the receive coils.

The housing portion may define a plurality of channel portions, each of which channel portions houses at least a portion of a respective receive coil from the plurality of receive coils.

The support structure may comprise a plurality of closing portions, each closing portion for blocking the mouth of a respective channel portion.

The plurality of channel portions may be defined in a one-piece portion of the housing portion.

The plurality of closing portions may be provided in a one-piece portion of the support structure.

In some cases the whole of the housing portion, or at least the whole of a part of the housing portion that defines coil receiving channels, may have a one-piece construction. In other cases the housing portion may be of a plurality of pieces, but yet a plurality of channel portions be defined in a one-piece part of the housing portion. In such a case there may be plural sets of channel portions, each set being defined in a respective one-piece part of the housing portion.

In some cases a one-piece portion of the support structure may comprise all of the closing portions. In other cases there may be plural sets of closing portions with each set of closing portions being provided in a respective one-piece portion of the support structure.

The housing portion may comprise a web of channel defining portions. Apertures through the housing portion may be provided between the channel defining portions.

The support structure may comprise a web of closing portions. Apertures through material making up the web of closing portions may be provided between the closing portions.

The web of channel defining portions and the web of closing portions may be dimensioned and arranged so as to register with one another such that respective closing portions in the web of closing portions are aligned or alignable with respective channels in the web of channel defining portions.

The provision of webs in the support structure can help enhance the provision a housing which facilitates adjustment of the positioning of carried receive coils.

The housing portion, or at least part of the housing portion, may be of resilient material. A part of the housing portion in the region of the or each channel may be of resilient material. The or each closing portion may be of resilient material.

The web of channel defining portions may be of resilient material. The web of closing portions may be of resilient material.

The use of resilient material in the housing portion and/or closing portion may facilitate push fitting of the closing portion into the closing position. The use of resilient material in the housing portion and/or closing portion may also facilitate shaping of at least part of the support structure, say cover portion, to conform with a body part with which the receive coil arrangement is designed to be used.

The use of resilient material in the housing portion and/or closing portion can help enhance the provision of a housing which facilitates adjustment of the positioning of carried receive coils. It noted that in some instances resilience may be provided or enhanced by the shape and configuration of components as well as the material of which they are made.

The housing portion may be additively manufactured.

The closing portion may be additively manufactured.

The cover portion may be additively manufactured.

The use additive manufacturing may be particularly advantageous when a web of channel defining portions and/or a web of closing portions is provided. Further, additive manufacturing can be convenient in providing support structures shaped and dimensioned to conform to a particular body part or even for a particular size of patient.

The housing portion may be of plastics material, say a thermoplastic, for example a thermoplastic polyurethane.

The closing portion may be of plastics material, say a thermoplastic, for example a thermoplastic polyurethane.

The cover portion may be of plastics material, say a thermoplastic, for example a thermoplastic polyurethane.

The at least one receive coil may comprise a length of co-axial cable, which may be arranged in a loop.

In some embodiments the receive coil arrangement comprises at least two receive coils, a first, main receive coil which is mounted on the base portion and a second, auxiliary, receive coil which comprises said at least a portion of the at least one receive coil which is provided in the receive coil housing portion, and the housing portion comprises the cover portion.

The main receive coil provided on the base portion may be more rigid than the auxiliary receive coil provided in the receive coil housing portion.

The auxiliary receive coil may comprise a length of co-axial cable which may be arranged in a loop.

The main receive coil may comprise a length of unshielded conductor.

Preferably the receive coil arrangement comprise a plurality of auxiliary receive coils.

According to another aspect of the invention there is provided a method of manufacturing an MRI system receive coil arrangement as defined above, the method comprising the steps of:
  making the housing portion;
  introducing the coil portion of the at least one receive coil into the channel portion of the housing portion; and
  moving the closing portion to the second position.

According to another aspect of the invention there is provided a method of manufacturing an MRI system receive coil arrangement as defined above, the receive coil arrangement comprising a plurality of receive coils and a respective plurality of closing portions and the method comprising the steps of:
  making the housing portion;
  introducing coil portions of the plurality of receive coils into the respective channel portions of the housing portion;
  moving the plurality of closing portions to the second position;
  checking the receiving operation of the receive coil arrangement; and
  where said checking indicates that a first predetermined standard of receiving operation has not been achieved, carrying out the further steps of:
    a) moving at least one of the closing portions back out of the second position;
    b) returning the at least one of the closing portions to the second position with the positioning of at least one of the receive coils adjusted;
    c) re-checking the receiving operation of the receive coil arrangement; and
    d) carrying out steps a) to c) in sequence until a second predetermined standard receiving operation is achieved.

The first and second predetermined standards of receiving operation may be the same as one another or different from one another—where they are different from one another, in different embodiments either may be set to be higher than the other.

The method may comprise the step of making the housing portion using an additive manufacturing process.

The method may comprise the step of making the closing portion using an additive manufacturing process.

According to another aspect of the invention there is provided a cover portion arrangement for use in a receive coil arrangement as defined above which cover portion arrangement comprises a plurality of receive coils of the receive coil arrangement and a cover portion which carries and supports each of the receive coils.

According to another aspect of the invention there is provided an MRI system comprising a main MRI scanner arrangement, a patient support, and an MRI system receive coil arrangement as defined above provided on the patient support and electrically connected to the main MRI scanner arrangement.

According to another aspect of the invention there is provided an MR-Linac system comprising an MRI system as defined above and a medical linear accelerator system.

According to another aspect of the invention there is provided a PET-MR system comprising an MRI system as defined above and a positron emission tomography system.

According to another aspect of the invention there is provided a stereotactic mask arrangement for treatment planning comprising an MRI system as defined above and a stereotactic mask to ensure the subjects position is well defined and transferable to stereotactic treatments using the same mask thereby guided by the MRI data.

Note that, in general terms and with any necessary modifications in wording, all of the further features defined above following any aspect of the invention above are applicable as further features of all other aspects of the invention defined above. These further features are not restated after each aspect of the invention merely for the sake of brevity.

BRIEF DESCRIPTION OF THE DRAWINGS

Embodiments of the present invention will now be described, by way of example only, with reference to the accompanying drawings in which.

DETAILED DESCRIPTION

Figure 1:
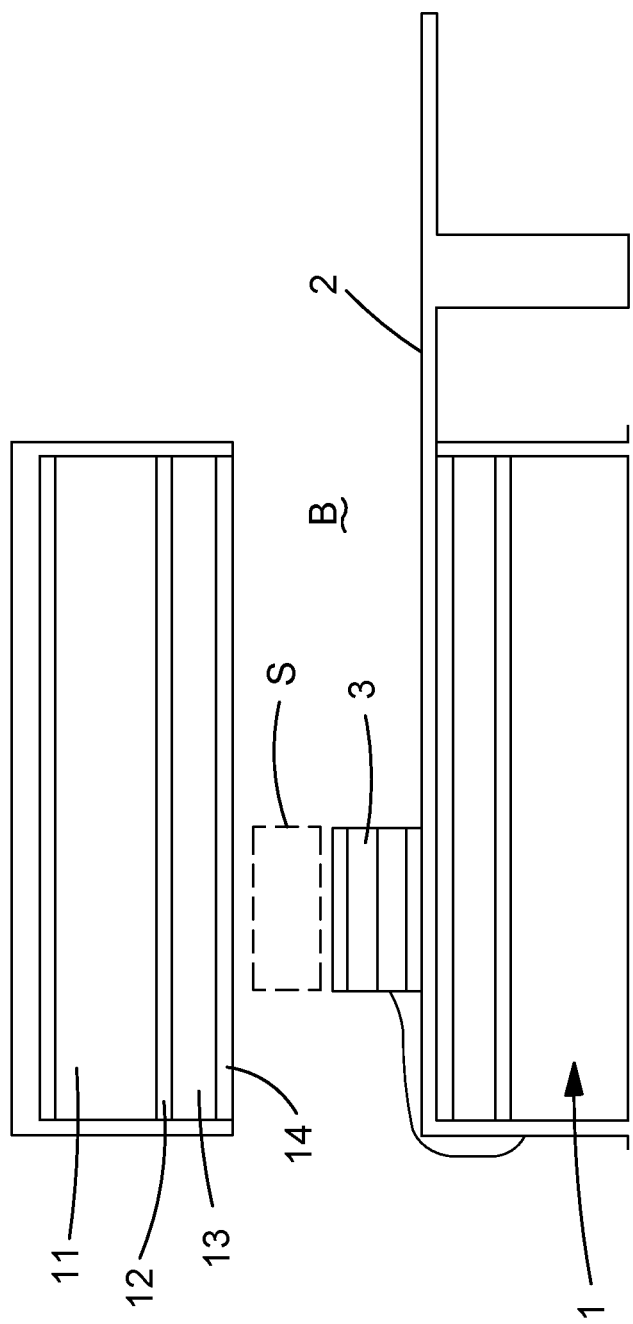
FIG. 1 schematically shows an MRI system including a receive coil arrangement.

FIG. 1 shows an MRI system comprising a main scanner arrangement 1, a patient support 2 which is arranged for supporting a patient when in the scanner arrangement 1 and an MRI system receive coil arrangement 3 which is separate from the main scanner arrangement and which in this embodiment is a body part specific receive coil arrangement. More generally such a receive coil arrangement 3 may be termed a local receive coil arrangement.

As alluded to above, in some instances an MRI system will be used in combination with other systems so as to provide for example, an MR-Linac system which comprises an MRI system and a medical linear accelerator system; or in another example, so as to provide a PET-MR system comprising an MRI system and a positron emission tomography system. In such a case, the MRI system shown in FIG. 1 may be supplemented by a linear accelerator system or positron emission tomography system S illustrated in dotted lines only in highly schematic form in FIG. 1. In another alternative the present system may be used in combination with a stereotactic mask S (again illustrated in dotted lines only in highly schematic form in FIG. 1) for stereotactic treatment/planning. The stereotactic mask being arranged to ensure the subject's position is well defined and transferable to stereotactic treatments using the same mask as well as the present receive coil arrangement 3 described herein such that the stereotactic treatments can thereby be guided by MRI data.

The main MRI scanner arrangement 1 may be an entirely conventional main MRI scanner arrangement comprising a main magnet 11 which will typically be a superconducting electromagnet, RF transmit coils 12, gradient coils 13 and main unit receive coils 14. These components are provided in a main body of the MRI scanner arrangement 1 which has a main bore B in which the patient support 2 is provided or, more typically, into which the patient support 2 can be moved carrying a patient until an operative position is reached.

At least in use the body part specific receive coil arrangement 3 is also provided in this main bore B. Where present at least part of a medical linear accelerator system or positron emission tomography system S may also be located in this main bore B during operation.

As well as being located in the main bore B of the main MRI scanner 1 during operation, the receive coil arrangement 3 is electrically connected to the main scanner arrangement 1 such that the magnetic resonance signals picked up by the receive coil arrangement 3 may be fed into the main scanner arrangement 1 for processing.

The signals picked up by the receive coil arrangement 3 may be used alone or in combination with signals picked up by the main unit receive coils 14 in processing and generating images. In some instances a main MRI scanner arrangement 1 without its own main unit receive coils 14 could be used with the present type of receive coil arrangement 3.

The structure and operation of MRI scanner arrangements is well developed and understood and the present ideas relate to the receive coil arrangement 3 for use with such an MRI scanner arrangement. Therefore, further description of the structure and operation of the MRI scanner arrangement 1 is not necessary and the remainder of this description relates to the receive coil arrangement 3.

Figure 2:
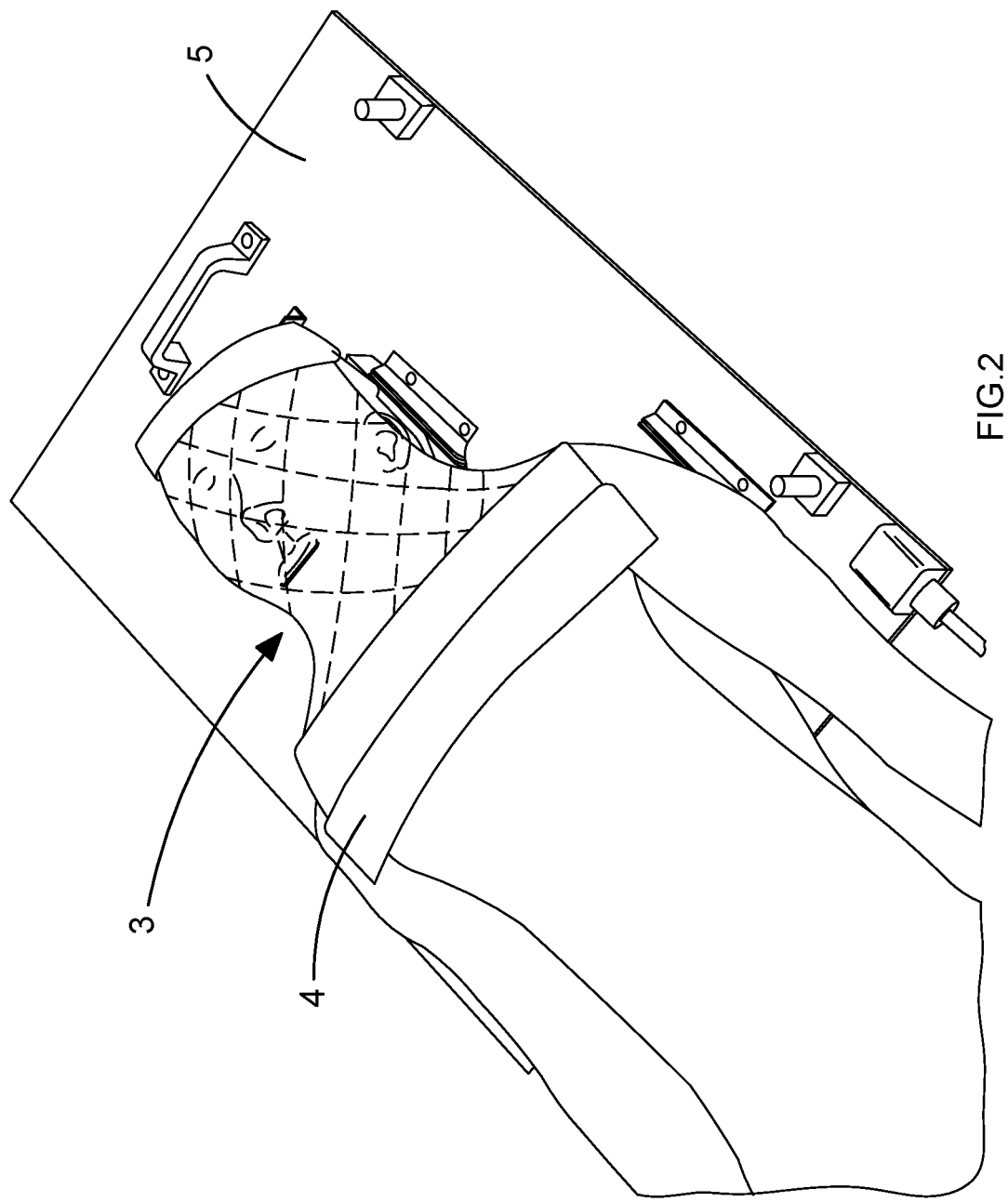
FIG. 2 schematically shows a receive coil arrangement, in highly schematic form, of the type included in the MRI system of FIG. 1 in position on a subject.
Figure 3:
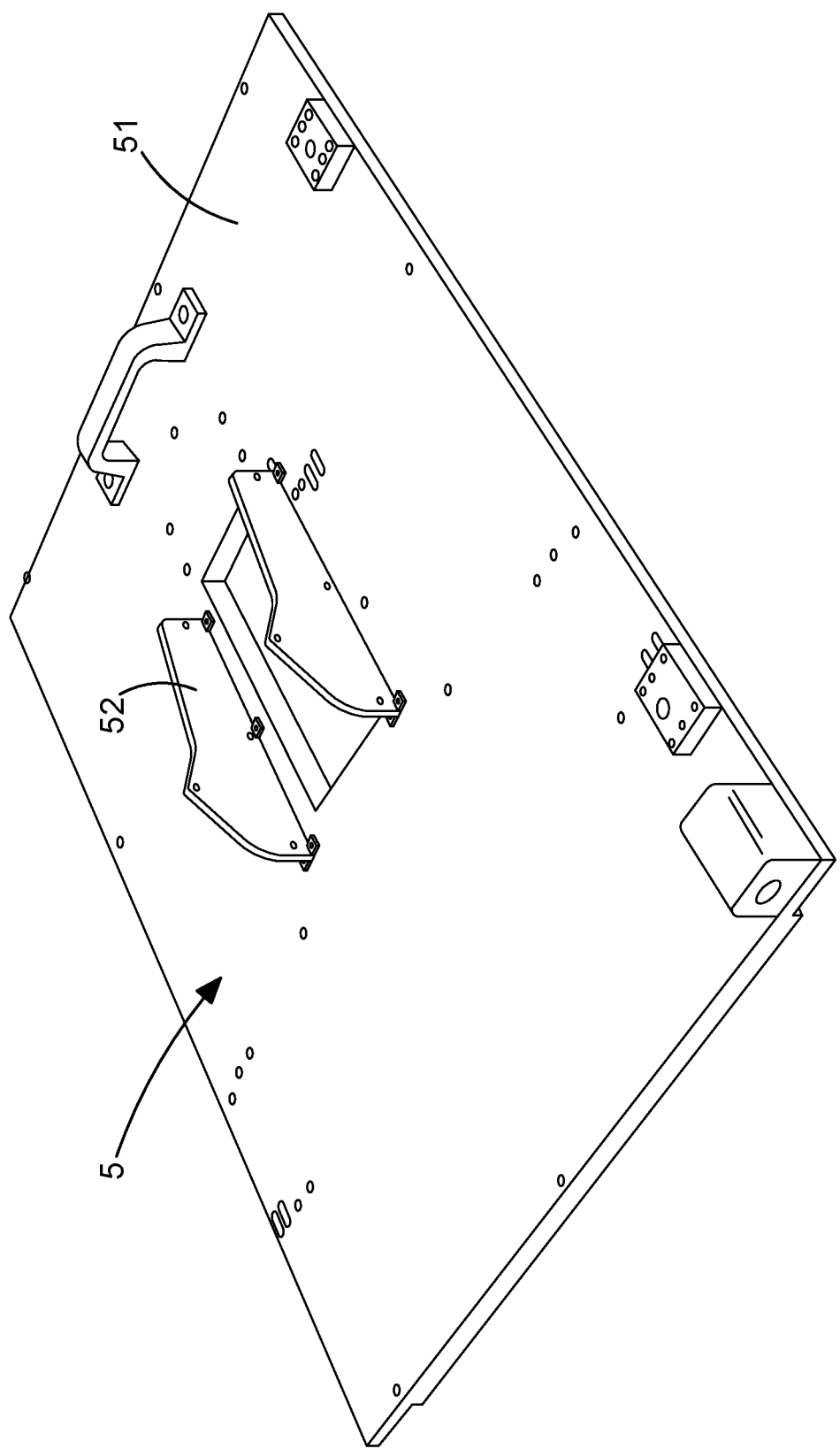
FIG. 3 schematically shows a base plate of the receive coil arrangement shown in FIG. 2.

FIG. 2 schematically shows the body part specific receive coil arrangement 3 in some more detail but still in schematic form. The body part specific receive coil arrangement 3 comprises a cover portion 4 and base portion 5. The base portion 5 is arranged to either be rested upon the patient support 2 or in some embodiments may be made to be an integral part of the patient support 2. On the other hand, the cover portion 4 is removably mounted on the base portion 5 so that it may be fitted over a subject and then secured in position on the base portion 5.

As may be seen by considering FIGS. 3 to 10 the body specific receive coil arrangement 3 comprises a primary receive coil 6 (see FIGS. 5 and 6) and a plurality of auxiliary receive coils 7 (see FIGS. 4 and 8 to 10). The base portion 5 is arranged for supporting the primary receive coil 6 and the cover portion 4 is arranged for supporting the auxiliary receive coils 7.

In this embodiment, the cover portion 4 and base portion 5 can be considered together to comprise support structure of the receive coil arrangement. The combination of the cover portion 4 and auxiliary receive coils 7 can be considered a cover portion arrangement. The combination of the base portion 5 and main receive coil 6 can be considered a base portion arrangement.

Note that whilst in the present embodiment, the receive coil arrangement comprises a base portion and a cover portion, in other embodiments this is not necessary. Thus, for example, the receive coil arrangement may comprise one support portion which may for example be arranged in the same way as the cover portion 4 in the present embodiment. Similarly there may be only one set of receive coils in other embodiments, which may comprise coils which correspond to the auxiliary coils 7 in the present embodiment.

Thus in an alternative embodiment the body specific receive coil arrangement 3 may comprise a cover portion arrangement 4,7 as described herein without a base portion arrangement as described herein.

Figure 6:
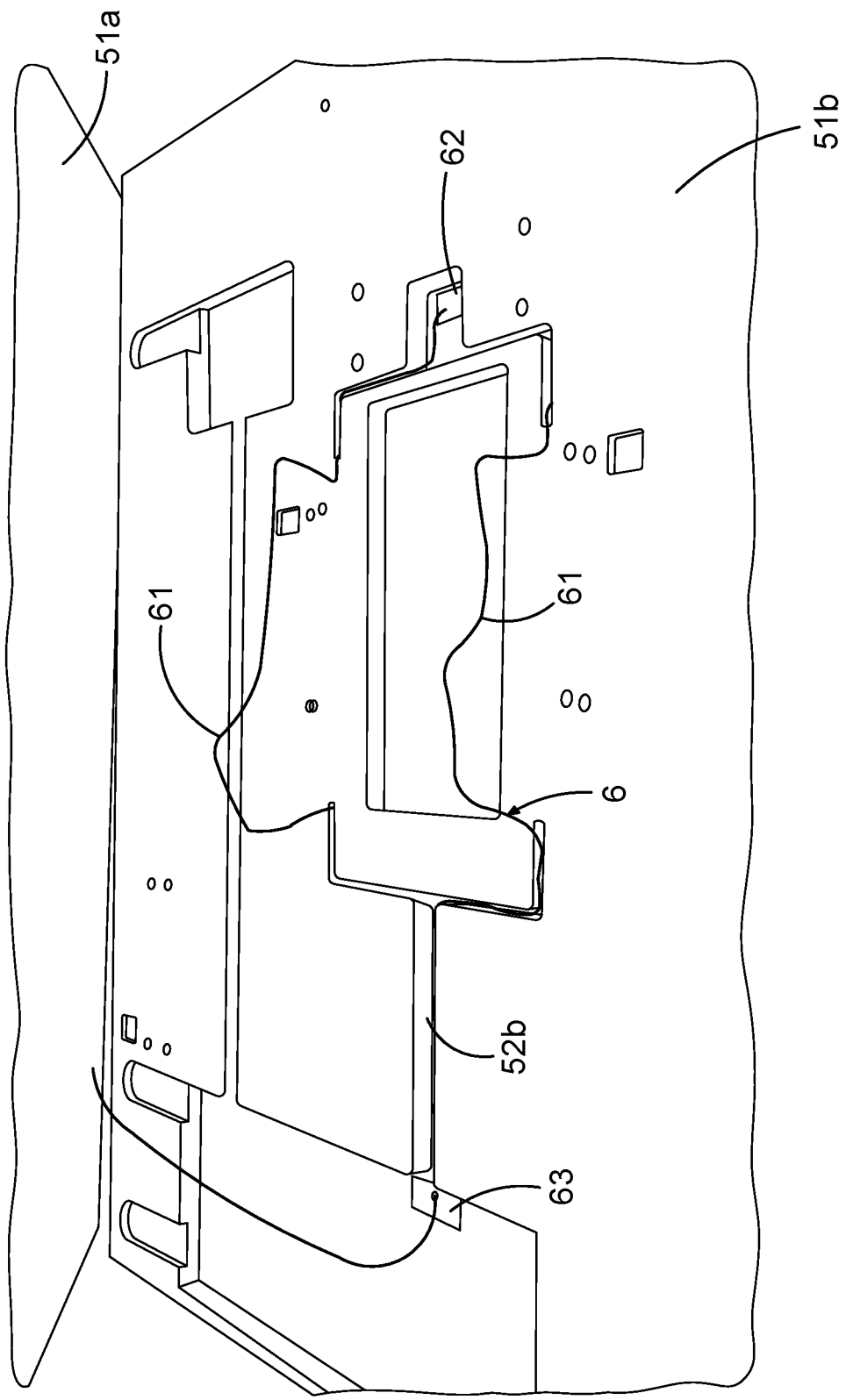
FIG. 6 shows the primary receive coil in the base plate but with part of the base plate removed.

The base portion 5 comprises a plate portion 51 and two upstanding portions 52. The upstanding portions 52 can be seen for example in FIGS. 3 and 5. The plate portion 51 has two layers 51a and 51b. The upstanding portions 52 are carried on the upper layer 51a as visible in FIGS. 3 and 5. In FIG. 6 the upper layer 51a is raised to show the lower layer 51b and to better show the primary receive coil 6.

The base portion 5 is provided with a plurality of channels 52a, 52b for supporting the primary receive coil 6 and holding it in a predefined position. A respective channel 52a (only one of which can be seen in the drawings i.e. in FIG. 5) is provided in each of the upstand portions 52 for holding a respective portion of the primary receive coil 6 in position in the upstand portion 52.

As will be appreciated by considering together for example, FIGS. 2, 3, 4 and 5, in use this portion of the primary receive coil 6 will be in close proximity to the subject, in particular the subject's head in the specific embodiment shown. The particular shape and path of the coil 6 is chosen to give desired receive characteristics for example to maximize penetration depth and ensure relatively constant electromagnetic coupling of energy to the tissue of the subject.

The lower layer 51b of the plate portion 51 includes respective channels 52b for holding the other parts of the primary receive coil 6 in position.

The primary receive coil 6 comprises unshielded lengths of conductor. In the present embodiment, two portions of unshielded conductor 61 are provided. The first of which runs in the channel 52a of the first of the upstands 52 and the second of which runs in the channel 52a of the other upstand 52. First ends of these conductor portions 61 are connected to a detune board 62 whilst other respective ends of the two conductor portions 61 are connected to a matching board 63. The detune board 62 and matching board 63 each comprise at least one electronic component, such as at least one tuning capacitor in the case of the matching board 63.

As seen in FIG. 6 the detune board 62 and matching board 63 are kept out of a central region of the coil 6, that is they are away from the location of the upstand portions 52 and those portions of the coil 6 which will be nearest a portion of interest in the subject. This creates an electronic component free zone in the region of interest of the subject. This is of particular interest where the body specific receive coil arrangement 3 is to be used in a combination system of the type described above where radiation is used in the combination system. Radiation may pass through this central region i.e. the region of interest in the subject without being adversely affected by the presence of electrical components and/or without risk of damage to such electrical components. Thus, this arrangement of the primary receive coil 6 helps the use of the present receive coil arrangement in systems such as PET-MR and MR-Linac systems.

The base portion 5, that is the plate portion 51 and the upstand portion 52 are of a relatively rigid plastics material for holding the primary receive coil 6 in a pre-defined position.

As alluded to above, this is important because alteration of the shape of the primary receive coil 6 will tend to affect tuning and matching that will negatively impact the sensitivity of the primary receive coil 6. The rigid construction and the coil's 6 shape and positioning have been chosen to minimise these effects.

Each of the auxiliary receive coils 7 has a different structure from the primary receive coil 6. Whilst the primary receive coil 6 is made of an unshielded conductor and has relatively low impedance, the auxiliary receive coils 7 are arranged as high impedance coils. In particular these coils 7 have higher impedance (as will be clear, what is referred to here is the magnitude of the impedance including both the resistive and reactive elements of the impedance) than that of the primary receive coil 6. Furthermore, the size of the auxiliary receive coils 7 is smaller than that of the primary receive coil 6, in particular the area which the auxiliary receive coils 7 bound is smaller than the area which the primary receive coil 6 bounds. This means that the primary receive coil 6 is better suited for receiving signals emanating from deep inside the subject whereas the auxiliary receive coils 7 are better suited for picking up signals emanating from a region of the subject close to the auxiliary receive coil 7 itself.

Further, due to the nature of the high impedance coils used for the auxiliary receive coils 7, they couple much less with their environment and thus the precise positioning is less important. This leads to the possibility of more accurately locating these auxiliary receive coils 7 in relation to a subject and allowing these receive coils 7 to conform to the shape necessary to put them into close contact with the relevant regions of interest in the subject.

Figure 7:
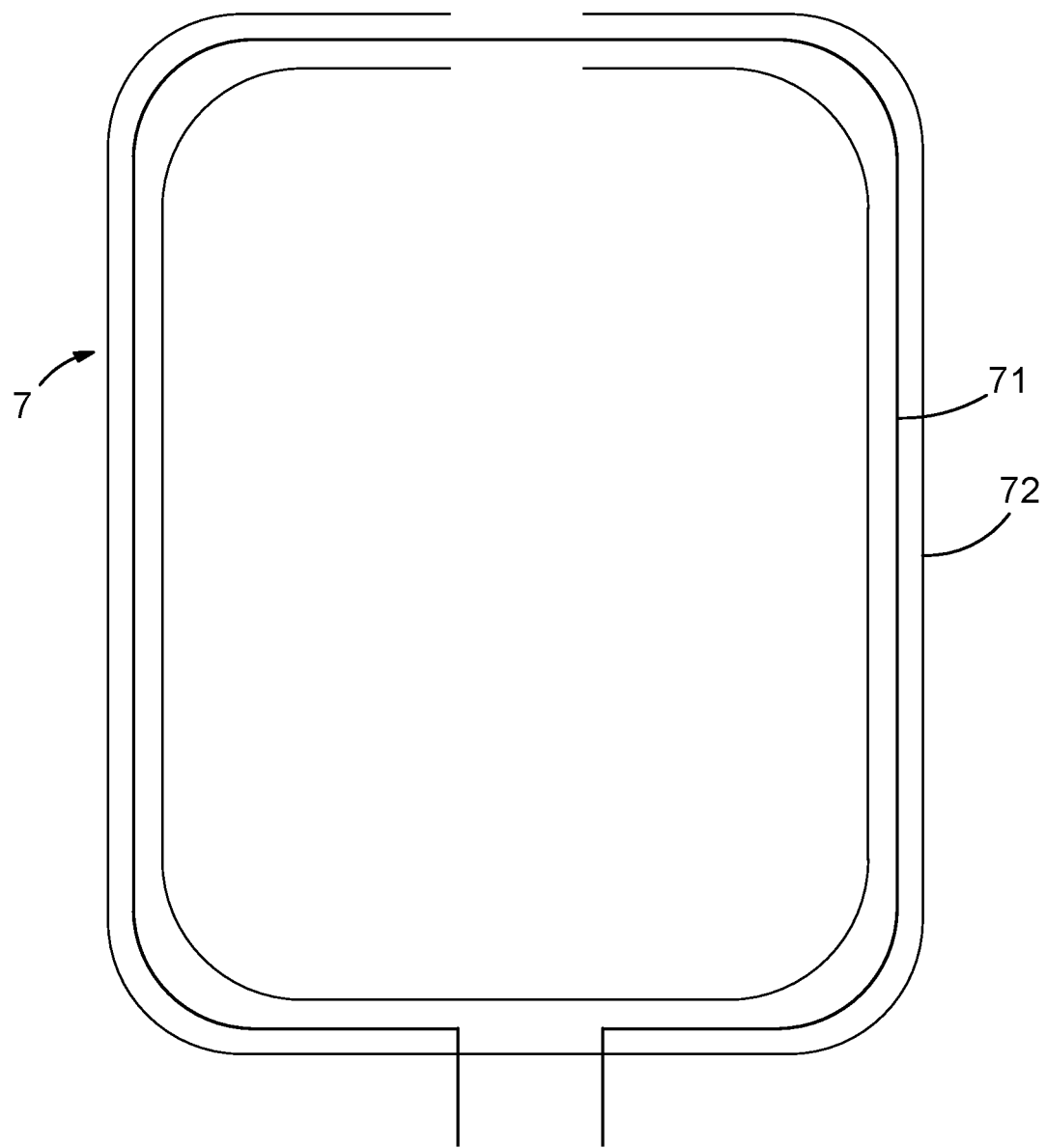
FIG. 7 schematically illustrates the connection arrangement of an auxiliary receive coil included in the receive coil arrangement shown in FIG. 2.

FIG. 7 schematically shows the connection arrangement of each of the auxiliary receive coils 7. Each auxiliary receive coil 7 is made out of a length of coaxial cable comprising a central conductor 71 and an outer shield conductor 72. In the receive coil the central conductor 71 is continuous around the coil and the ends of the central conductor 71 are connected to a respective matching board 73 (see FIG. 4). On the other hand, the shield conductor 72 is provided with a gap at a location remote from the ends of the inner conductor 71 whilst the two ends of the shield 72 near the ends of the inner conductor 71 are connected together. The matching boards 73 each comprise at least one electronic component, such as at least one tuning capacitor.

Due to the nature of the high impedance coils, the total length of each coaxial cable that defines the coil is restricted to close proximity to a half wavelength, thereby limiting the overall size of the auxiliary receive coils 7.

In the present embodiment the cover portion 4 arrangement comprises a coil housing portion 43 which comprises a lattice work or web 40 of support members 41. Open apertures 42 are defined between the support members 41. Thus overall the cover portion 4 is very open and includes a minimised amount of support material. This can help save material, make the cover portion more acceptable/comfortable for a patient, and can help in achieving good radio transparency characteristics.

The coil housing portion 43 and in particular the web 40 of support members 41 supports each of the auxiliary receive coils 7 in a respective desired location. The support members 41 in the present embodiment are of two kinds. There are first support members 41a which house portions of the receive coils 7 (see FIG. 9) and second support members 41b which do not house coil portions but help to support the first support members 41a in the overall web 40 of support members 41.

Figure 4:
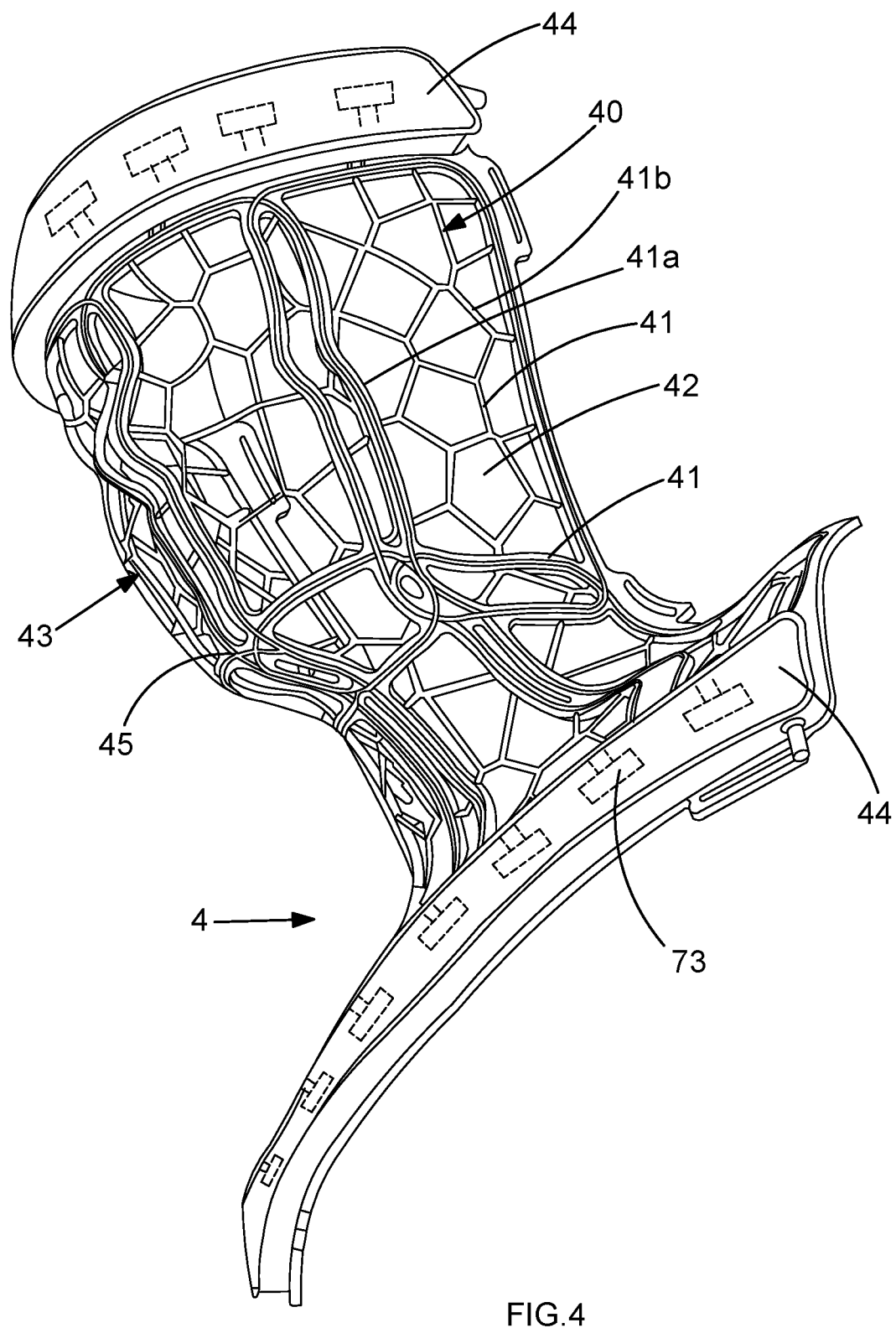
FIG. 4 schematically shows a cover portion arrangement of the receive coil arrangement shown in FIG. 2.
Figure 5:
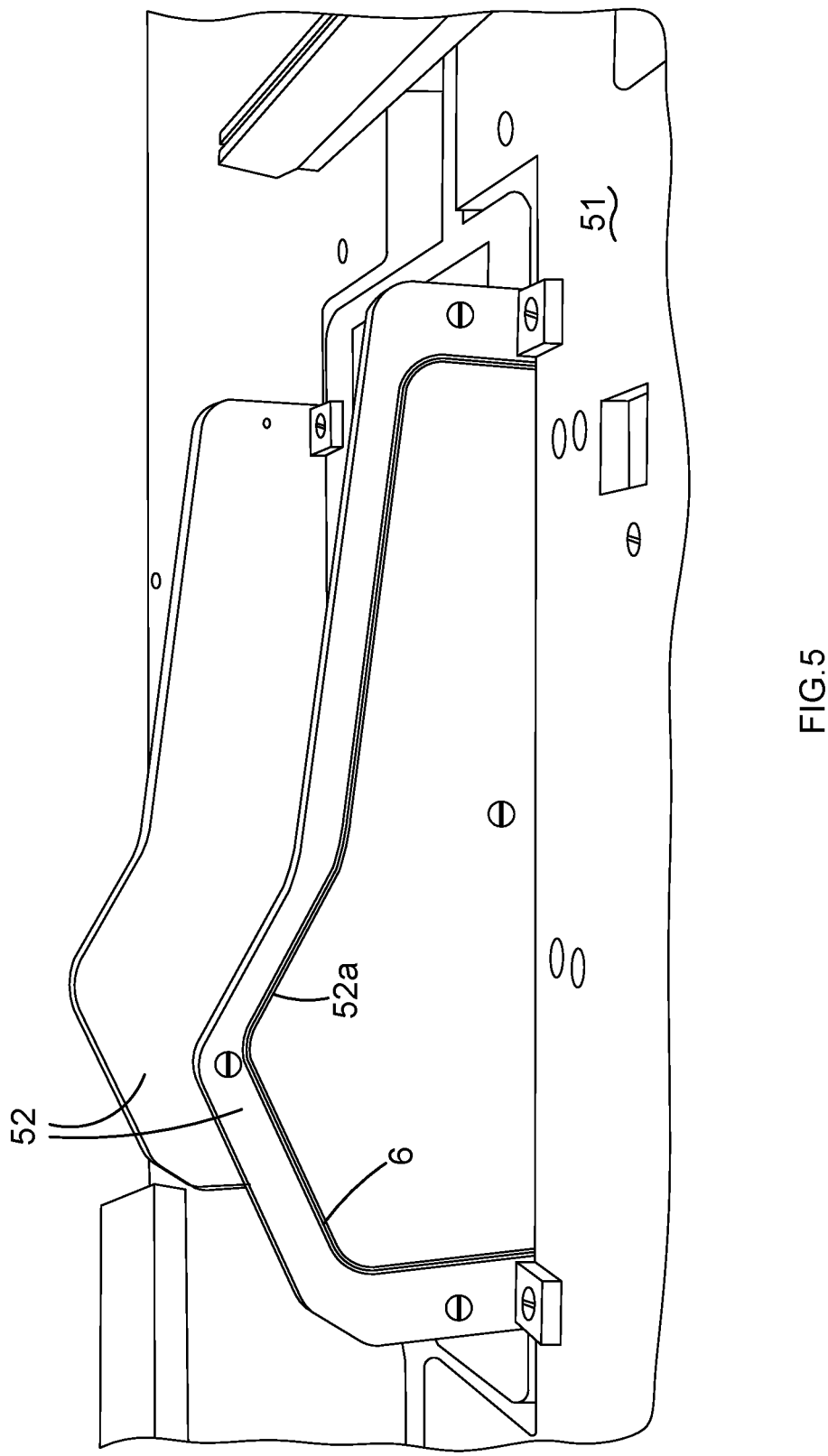
FIG. 5 shows in more detail part of the base plate shown in FIG. 3 which part is arranged for receiving a primary receive coil.

The cover portion 4 further comprises at least one terminal housing portion 44 (in the present embodiment there are two terminal housing portions 44)—see FIG. 4—to which the ends of the auxiliary coils 7 lead and which house the respective matching boards 73.

The receive coil housing portion 43 comprises a plurality of channel portions 43a each of which holds a respective portion of at least one of the auxiliary coils 7. The location of the auxiliary coil 7 in the channel portion 43a helps hold the respective auxiliary coil 7 in position.

Each channel portion 43a comprises a respective mouth 43b, through which the auxiliary coil 7 can be introduced into the channel 43a.

The cover portion 4 further comprises a web 45 of closing portions 45a. Each closing portion 45a is arranged to be push fitted into a mouth 43b of a respective channel portion 43a to block the mouth 43b and hence cover and help retain the auxiliary coil 7 which is located in the respective channel portion 43a.

Figure 10:
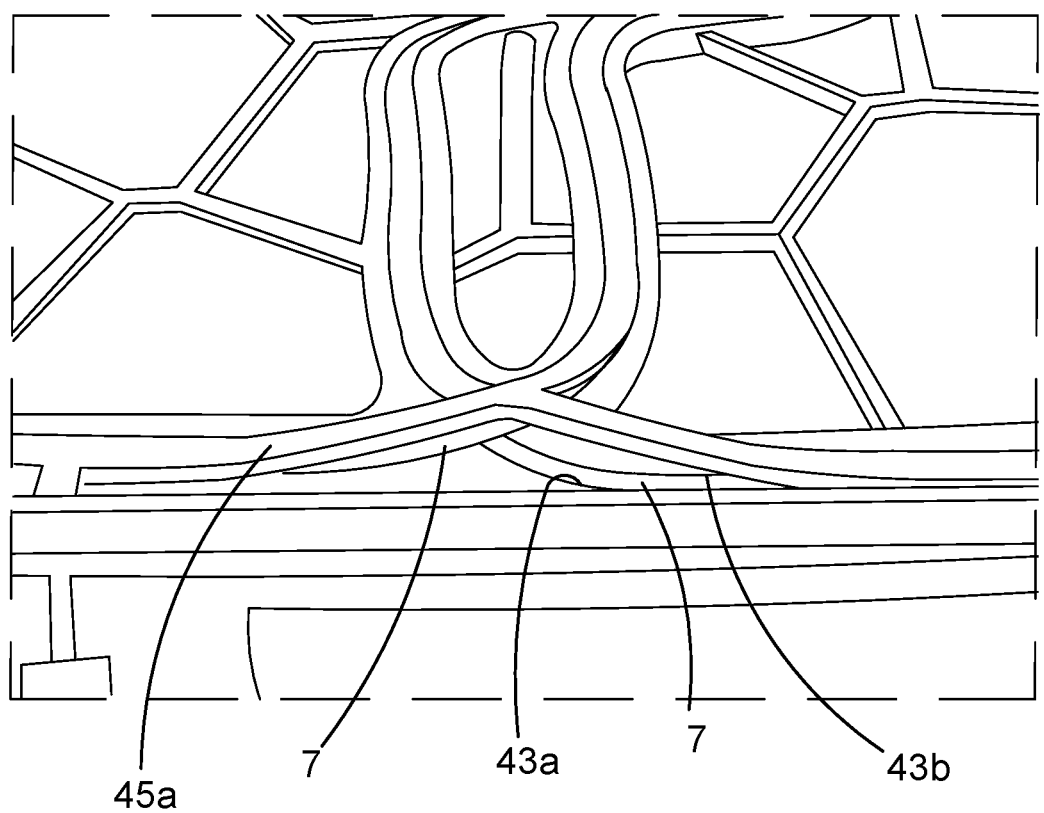
FIG. 10 shows a detail of the cover portion arrangement of FIGS. 4, 8 and 9 with a closing portion of the cover portion arrangement partially inserted into a housing portion of the cover portion arrangement.

FIG. 10 shows part of the web 45 of closing portions 45a when partially push fitted into respective mouths 43b of the receive coil housing portion 43.

In the present embodiment the closing portions 45a are arranged to completely fill the respective mouths 43b of all of the channel portions 43a. Together the channels 43a of the coil housing portion 43 and closing portions 45a in the present embodiment surround and encase the auxiliary coils 7. In combination the terminal housing portions 44, the coil housing portion 43 and closing portions 45a in the present embodiment completely encase the auxiliary coils 7 and associated matching boards 73. In the present embodiment no part of the auxiliary coils 7 is exposed or indeed visible in the assembled cover portion.

This is achieved without the need for processing of the support structure after the coils 7 are provided in position and without the need for adhesive or use of a coating material such as foam.

Figure 9:
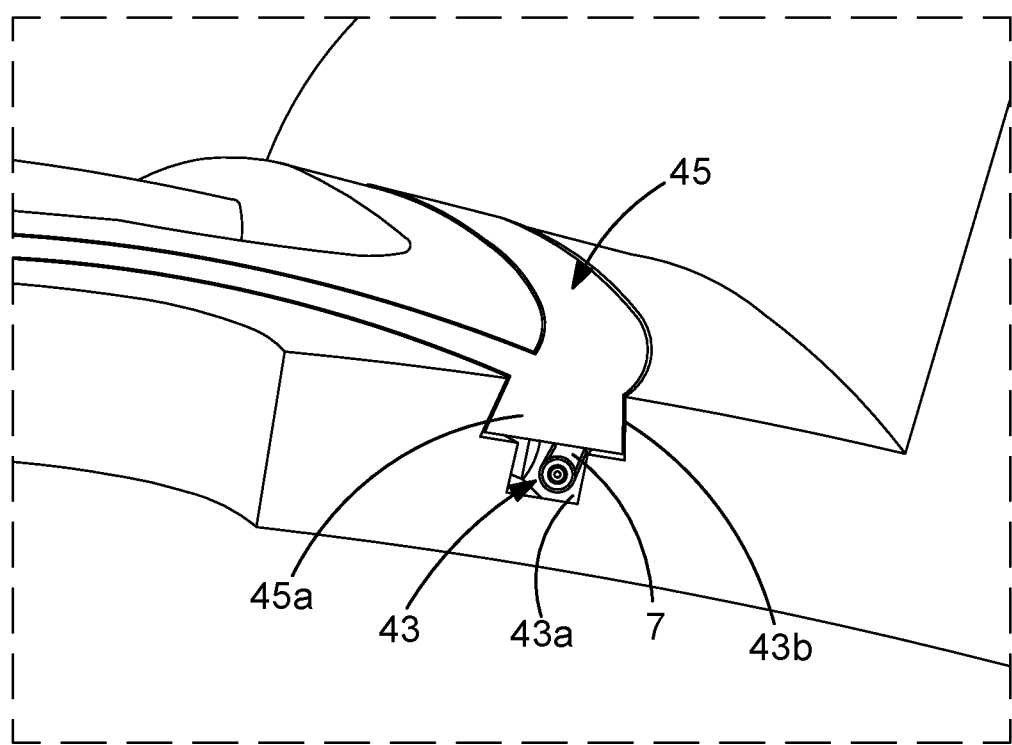
FIG. 9 shows a detail IX of the section shown in FIG. 8 with a coil portion of an auxiliary receive coil located in a channel portion of the cover portion arrangement.

The closing portions 45a and mouths 43b are arranged to engage with one another to when push fitted into a closing position as shown in FIG. 9 from a first, open, position as partially shown in FIG. 10. This engagement resists movement of the closing portions 45a back out of the closing position but does not prevent it. Thus the closing portions 45a are releasably locked or latched into the second, closing, position.

Each mouth 43b has a re-entrant shape in cross-section as can be seen in FIG. 9 and each closing portion 45a has a correspondingly shaped insertion portion which engages with the re-entrant shaped mouth when the closing portion 45a is pushed into the mouth 43b.

The material of the closing portions 45a and/or housing portion 43 is selected to be sufficiently resilient to allow this latching of the components together.

In the present embodiment the web 40 of support members and web 45 of closing portions are of a thermoplastic polyurethane. This can provide suitable resilience for the above described mouth closing system.

The relative flexibility of the web 40 of support members and web 45 of closing portions as well as the relative flexibility of the auxiliary receive coils 7 can provide advantages. The cover portion arrangement 4, 7 is significantly more flexible than the base portion arrangement 5, 6.

As the webs 40, 45 are flexible, the auxiliary coils 7 are flexible, and the auxiliary coils 7 can operate effectively when taking up a desired position this means that the cover portion 4 can be designed to closely fit the area of a subject which is of interest. Further the cover portion arrangement 4, 7 may be flexed to some degree when being used with an individual patient, which can help allow positioning of the auxiliary coils 7 in an optimal position for the patient.

The flexibility of the arrangement plus the releasably lockable nature of the support structure gives another possibility.

When assembling the cover portion arrangement 4, 7, the appropriate receive coils 7 are introduced into the respective channel portions 43a and then the closing portions 45a are push fitted into place. The interaction of the housing portion 43, closing portions 45a and their interlocking serves to stiffen up the cover portion 4 to some degree. Because there is flexibility in the arrangement, the precise way that the closing portions 45a are push fitted into place will subtly affect the relative positioning of the receive coils 7 supported in the cover portion 4 in this stiffened interlocked condition. This in turn can have an impact on the receive characteristics of the receive coil arrangement as a whole.

Thus when the closing portions 45a have been put in their closing positions, the receive characteristics may be checked (ie by using the receive coil arrangement in combination with an MRI machine to scan a test object or "phantom"). If these differ from what is expected and/or there is a desire to optimise performance, at least one of the closing portions 45a may be moved back out of the second, closing, position and then reclosed so as to subtly move one or more of the auxiliary coils 7 relative to the others. After this the receive characteristics may be checked again. This process can then be stopped or continued until a desired level of receive performance is obtained.

The web 40 of support members and web 45 of closing portions are additively manufactured (for example "3D printed") in the present embodiment. This facilitates producing a support structure that can be shaped and dimensioned to conform with a selected body part.

In alternatives different types of closing portions may be provided. First the closing portions may be made integral with or at least connected to the housing portion even when in the first, open, position. Second, irrespective of the above, a different type of closing approach may be taken in alternatives where the closing portion has two parts which can be push fitted together above or across the mouths of the housing portion to cover and/or retain a housed receive coil portion.

In the present embodiment the web 45 of closing portions 45a is in one piece and includes a respective closing portion 45a for each channel portion 43a in the receive coil housing portion 43. In alternatives however, individual closing portions 45a, or a plurality of webs 45 of closing portions 45a might be provided. Similarly in alternatives a plurality of webs 40 of support members 41 might be provided.

In the present embodiment the cover portion 4 is arranged for location on the head, face and neck of a patient. It correspondingly includes portions of the cover for covering the head, face and neck of the subject when in position.

Figure 8:
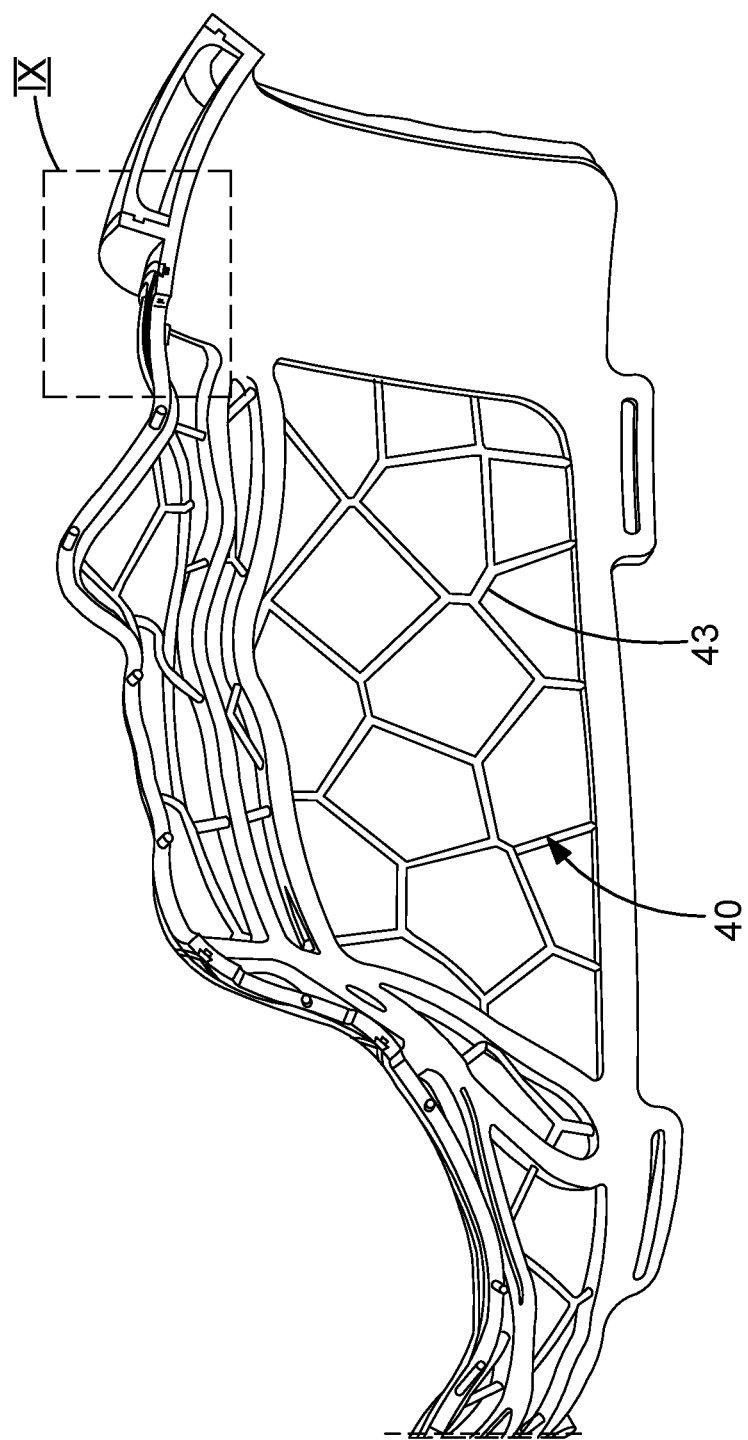
FIG. 8 shows a section through the cover portion arrangement shown in FIG. 2.
Figure 11A:
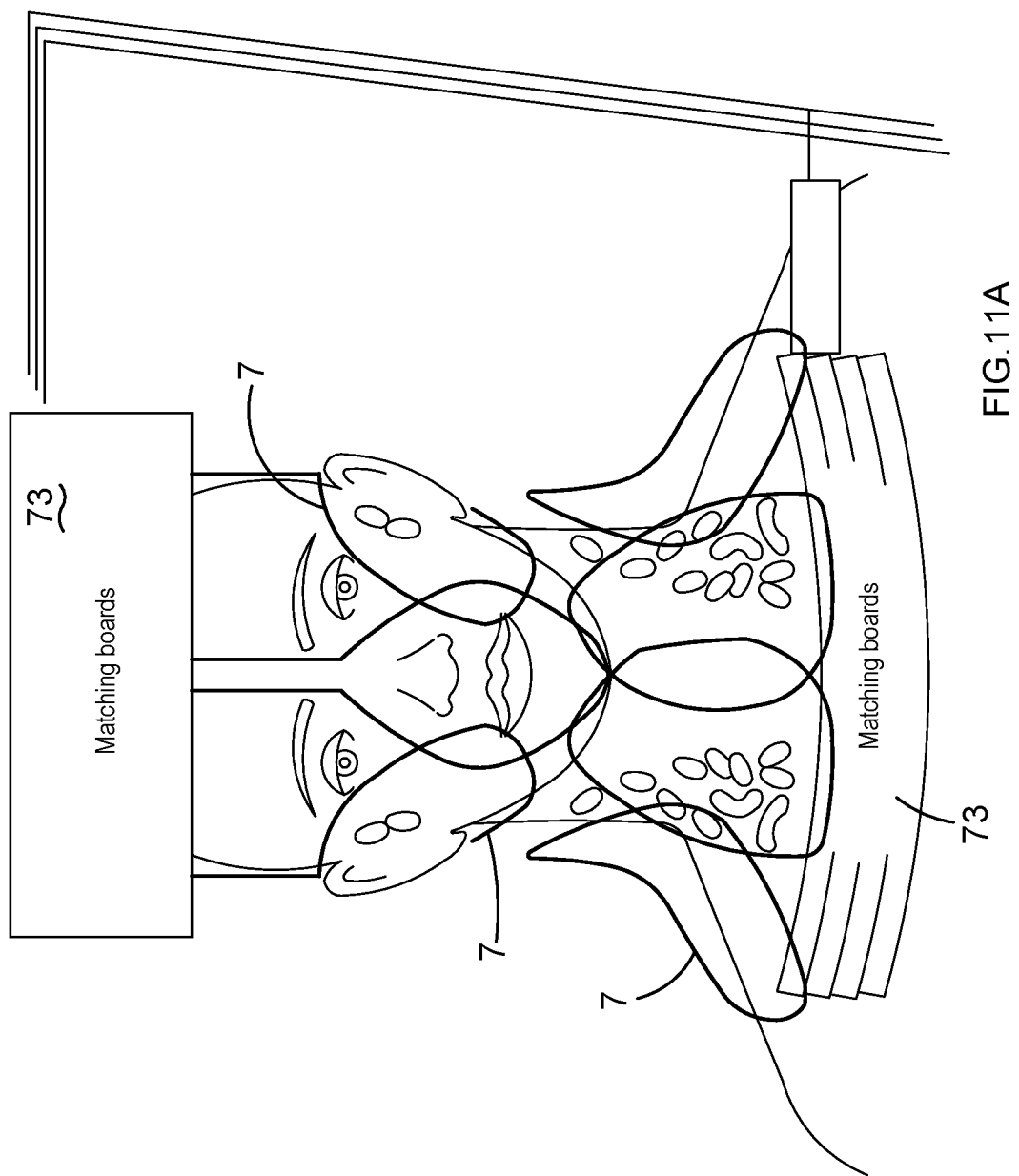
FIGS. 11A and 11B respectively show a front view and side view schematic of the primary and auxiliary coils of the receive coil arrangement of the type shown in FIG. 2 when positioned around a subject.
Figure 11B:
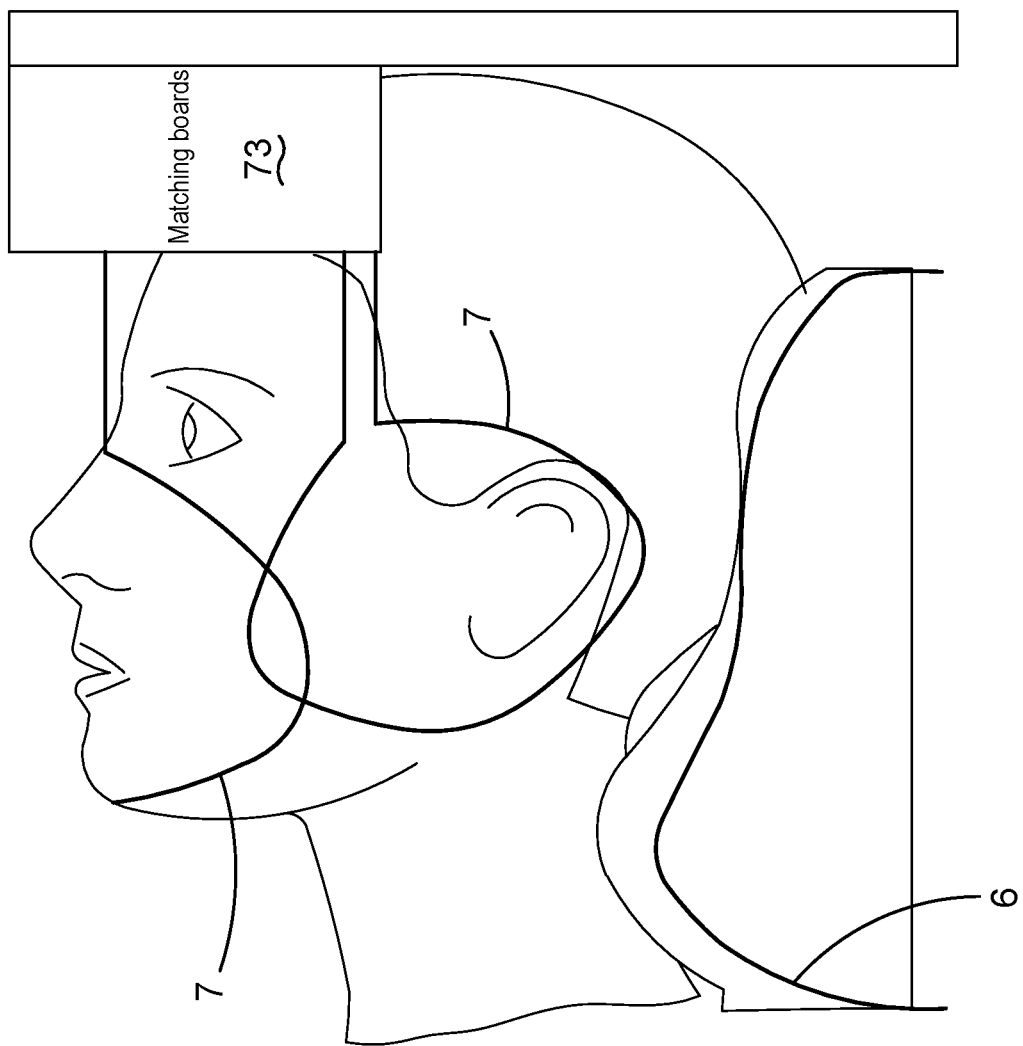

The locations of the primary coil 6 and auxiliary coils 7 in relation to a subject when the subject is positioned on the base portion 5 and cover portion 4, of the same general kind as shown in FIGS. 8 to 10 is in position, may be best seen in FIGS. 11A and 11B. Note that the actual set of auxiliary coils 7 illustrated in FIGS. 11A and 11B is different in number and/or arrangement from that included in the cover portion arrangement 4, 7 shown in FIGS. 8 to 10, but the overall effect is similar, and it will be noted that various different forms of cover portion arrangements 4, 7 and receive coil arrangements can embody the present invention.

In this instance, the primary coil 6 can be seen located in the region of the patient's head. The primary coil 6 has greater facility for acquiring data from a greater depth within the subject. This receive coil 6 may usefully pick up signals generated from any region within the patient's head and neck.

On the other hand, the auxiliary coils 7 (both in the arrangement shown in FIGS. 4 & 8 to 10 and the arrangement shown in FIGS. 11A and 11B) are located at differing locations over the patient's face and neck. There is partial overlapping between each auxiliary coil 7 but largely each auxiliary coil 7 is looking to pick up signals from a different area of face and neck of the subject.

In the arrangement shown in FIGS. 11A and 11B there are seven auxiliary coils 7, three of which are arranged for location over a subject's face and four of which are arranged for location over a subject's neck and shoulder.

Correspondingly, if one thinks of the cover portion 4 as illustrated for example, in FIG. 2, four of auxiliary coils 7 are provided on the neck covering portion of the cover and three of the auxiliary coils 7 are provided on the face covering portion of the cover 4.

The auxiliary coils 7 are arranged, in both in the arrangement shown in FIGS. 4 & 8 to 10 and the arrangement shown in FIGS. 11A and 11B, to overlap each other by in the region of 10-15% to further reduce residual inductive coupling.

Again, in both cases the matching boards 73 for the auxiliary coils 7 are kept out of the central region i.e. the region of interest in the subject so that there is an electronic component free zone giving the benefits described above.

Note that the flexible design of the cover 4 as well as the fact that the auxiliary coils 7 are tolerant to being provided in different positions and bent into slightly different shapes, facilitates the provision of a cover portion arrangement 4, 7 which may be used over a mask or other jig which needs to be used in a combined system. For example, in a MR-Linac system where a patient specific immobilization mask or jig is provided for appropriately directing the radiation used in the radiotherapy to be delivered by the MR-Linac system, a cover portion 4 of the present kind may be used in conjunction with that existing mask or jig without needing to modify it. Further of course using additive manufacturing—eg 3D printing—allows production in almost any shape configuration. The receive coil arrangement or at least the cover portion arrangement will typically be flexible—ie deformable in use or fitting by an operator. Moreover the receive coil arrangement can be made lightweight and/or can be made wearable.

As well as more conventional MRI, MR-Linac and PET MR as mentioned above, the present type of receive coil arrangement is also suitable for use in MR Sim (Simulation) systems and in general can be designed for use with pretty much all MR/MRI systems using different fields/radiation/particles since a relatively low volume of material can be used in the support structure, or at least the cover portion, and there is freedom in choice of the material to be used—thus for example good radio-translucent or radio-transparent properties can be obtained.

Figure 12:
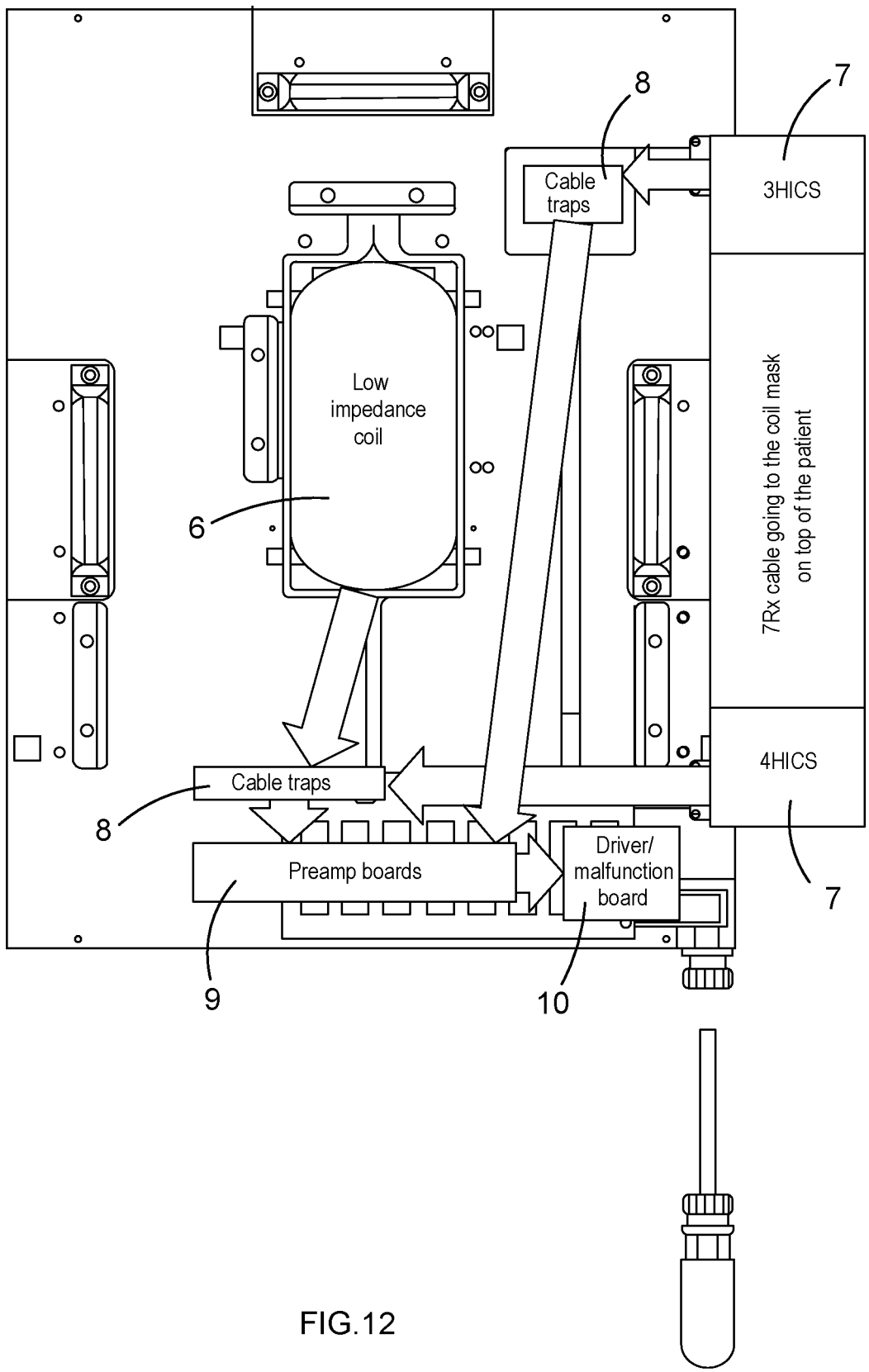
FIG. 12 is a schematic showing connections between various components in the receive coil arrangement shown in FIG. 2.

FIG. 12 is a schematic showing the overall connection arrangement of the receive coil arrangement shown in FIGS. 2-10. The low impedance primary coil 6 and the high impedance auxiliary coils 7 are connected via appropriate cable traps 8 to preamp boards 9, the output of which is fed to a driver malfunction board 10 and the output of this becomes the output of the receive coil arrangement 3 as a whole for feeding into the main MRI scanner arrangement 1.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. An MRI system receive coil arrangement for use with a main MRI scanner arrangement, the receive coil arrangement comprising support structure and at least one receive coil carried on the support structure, wherein the support structure comprises:
   a receive coil housing portion which defines a channel portion which houses at least a portion of the at least one receive coil, said channel having a mouth for allowing the introduction of said at least a portion of the at least one receive coil through the mouth and into the channel; and
   a closing portion moveable between a first position in which the mouth of the channel portion is open for allowing introduction of said at least a portion of the at least one receive coil into the channel portion and a second, closing, position in which the mouth of the channel is blocked by the closing portion, wherein the housing portion defines a plurality of a channel portions, each of which channel portions houses at least a portion of a respective receive coil from the at least one receive coil, and the housing portion comprises a web of channel defining portions.

2. The MRI system receive coil arrangement as claimed in claim 1 in which the closing portion is a push fit closing portion which is push fittable into the second, closing, position from the first position.

3. The MRI system receive coil arrangement according to claim 1 in which the support structure is arranged so that the closing portion is locked against movement back towards the first position once moved into the second position.

4. The MRI system receive coil arrangement according to claim 3 in which the support structure is arranged so that the closing portion is releasably locked against movement back towards the first position once moved into the second position.

5. The MRI system receive coil arrangement according to claim 1 in which the closing portion is arranged to be a push fit with the housing portion, such that in moving the closing portion to the closing position, the closing portion is push fitted into position on the housing portion and blocks the mouth of the channel portion.

6. The MRI system receive coil arrangement according to claim 5 in which the closing portion is a push fit with the mouth of the of the channel portion.

7. The MRI system receive coil arrangement according to claim 5 in which the closing portion is arranged to be push fittable into the mouth.

8. The MRI system receive coil arrangement according to claim 5 in which the closing portion and the housing portion are arranged so that the closing portion is locked against movement back towards the first position once push fitted into position on the housing portion.

9. The MRI system receive coil arrangement according to claim 5 in which the mouth of the channel portion has a receiving region which has a re-entrant shape in cross-section and the closing portion comprises a correspondingly shaped insertion portion which fits in the receiving region when the closing portion is push fitted into the mouth.

10. The MRI system receive coil arrangement according to claim 1 in which the closing portion is a separate component from the housing portion.

11. The MRI system receive coil arrangement according to claim 1 in which the housing portion is shaped so as to conform with a predetermined body part.

12. The MRI system receive coil arrangement according to claim 1 in which the support structure comprises a base portion and a cover portion, wherein the base portion is more rigid than the cover portion and the cover portion comprises said receive coil housing portion.

13. The MRI system receive coil arrangement according to claim 1 which comprises a plurality of receive coils carried on the support structure and the receive coil housing portion houses a plurality of the receive coils.

14. The MRI system receive coil arrangement according to claim 1 in which the plurality of channel portions are defined in a one-piece portion of the housing portion.

15. The MRI system receive coil arrangement according to claim 1 in which the support structure comprises a plurality of closing portions, each closing portion for blocking the mouth of a respective channel portion.

16. The MRI system receive coil arrangement according to claim 15 in which the plurality of closing portions are provided in a one-piece portion of the support structure.

17. The MRI system receive coil arrangement according to claim 15 in which the support structure comprises a web of closing portions.

18. The MRI system receive coil arrangement according to claim 17 in which the housing portion comprises a web of channel defining portions and the web of channel defining portions and the web of closing portions are dimensioned and arranged so as to register with one another such that respective closing portions in the web of closing portions are aligned or alignable with respective channels in the web of channel defining portions.

19. The MRI system receive coil arrangement according to claim 1 in which the housing portion additively manufactured.

20. The MRI system receive coil arrangement according to claim 1 in which the closing portion is additively manufactured.

21. The MRI system receive coil arrangement according to claim 1 in which the at least one receive coil comprises a length of co-axial cable arranged in a loop.

22. An MRI system comprising a main MRI scanner arrangement, a patient support, and an MRI system receive coil arrangement as claimed in claim 1 provided on the patient support and electrically connected to the main MRI scanner arrangement.

23. An MR-Linac system comprising an MRI system as claimed in claim 22 and a medical linear accelerator system.

24. A PET-MR system comprising an MRI system as claimed in claim 22 and a positron emission tomography system.

25. A stereotactic mask-MR system for treatment planning comprising an MRI system as claimed in claim 22 and a stereotactic mask that can be used for MR guided treatments.

26. An MRI system receive coil arrangement for use with a main MRI scanner arrangement, the receive coil arrangement comprising support structure and at least one receive coil carried on the support structure, wherein the support structure comprises:
  a receive coil housing portion which defines a channel portion which houses at least a portion of the at least one receive coil, said channel having a mouth for allowing the introduction of said at least a portion of the at least one receive coil through the mouth and into the channel; and
  a closing portion moveable between a first position in which the mouth of the channel portion is open for allowing introduction of said at least a portion of the at least one receive coil into the channel portion and a second, closing, position in which the mouth of the channel is blocked by the closing portion, wherein the support structure comprises a plurality of closing portions, each closing portion for blocking the mouth of a respective channel portion, and the support structure comprises a web of closing portions.

27. An MRI system receive coil arrangement for use with a main MRI scanner arrangement, the receive coil arrangement comprising support structure and at least one receive coil carried on the support structure, wherein the support structure comprises:
  a receive coil housing portion which defines a channel portion which houses and holds in position at least a portion of the at least one receive coil, said channel having a mouth for allowing the introduction of said at least a portion of the at least one receive coil through the mouth and into the channel; and
  a closing portion moveable between a first position in which the mouth of the channel portion is open for allowing introduction of said at least a portion of the at least one receive coil into the channel portion and a second, closing, position in which the mouth of the channel is blocked by the closing portion,
  wherein a plurality of receive coils are carried on the support structure and the receive coil housing portion houses a plurality of the receive coils, and
  the housing portion defines a web of channel defining portions providing a plurality of channel portions, with each channel portion housing at least a portion of a respective receive coil from the plurality of receive coils, and with apertures being provided between the channel defining portions.

* * * * *